United States Patent [19]

Punja

[11] 4,325,966

[45] Apr. 20, 1982

[54] FUNGICIDAL COMPOUNDS, COMPOSITIONS AND PROCESSES

[75] Inventor: Nazim Punja, Crowthorne, England

[73] Assignee: Imperial Chemical Industries Limited, London, England

[21] Appl. No.: 34,134

[22] Filed: Apr. 27, 1979

[30] Foreign Application Priority Data

| May 15, 1978 | [GB] | United Kingdom | 19566/78 |
| Jun. 22, 1978 | [GB] | United Kingdom | 27613/78 |
| Dec. 18, 1978 | [GB] | United Kingdom | 48901/78 |
| Dec. 18, 1978 | [GB] | United Kingdom | 48975/78 |
| Mar. 19, 1979 | [GB] | United Kingdom | 09485/79 |

[51] Int. Cl.$^3$ ............... A01N 37/22; A01N 43/08; C07C 103/365; C07D 307/68
[52] U.S. Cl. ............... 424/285; 260/347.3; 260/347.4; 424/300; 424/309; 424/32; 560/24; 560/27; 560/29; 560/30; 560/43; 564/202
[58] Field of Search ............ 260/347.3, 347.4, 562 R, 260/562 A, 562 P; 560/43; 424/285, 309, 324; 564/202

[56] References Cited

U.S. PATENT DOCUMENTS

| 2,384,811 | 9/1945 | Coleman et al. | 260/562 R X |
| 3,048,619 | 8/1962 | Pray | 560/24 |
| 3,249,625 | 5/1966 | Bestian et al. | 260/562 R X |
| 3,268,583 | 8/1966 | Moore et al. | 260/562 R X |
| 3,274,170 | 9/1966 | Ugi et al. | 260/562 R X |
| 4,013,684 | 3/1977 | Merkle et al. | 260/347.3 |
| 4,021,224 | 5/1977 | Pallos et al. | 260/347.3 X |

FOREIGN PATENT DOCUMENTS 10673 10/1979 European Pat. Off. .

*Primary Examiner*—Richard Raymond
*Attorney, Agent, or Firm*—Cushman, Darby & Cushman

[57] ABSTRACT

This invention relates to alkenyl and alkynyl acylanilide derivatives useful as pesticides, especially as fungicides, to a process for preparing them, to pesticidal compositions containing them, and to a method of combating pests using them.

9 Claims, No Drawings

FUNGICIDAL COMPOUNDS, COMPOSITIONS AND PROCESSES

The invention provides a process for combating pests, especially fungi, which comprises applying to plants or seeds, or to their loci, an acylanilide derivative having the formula:

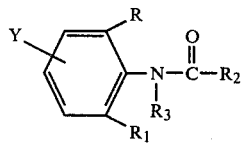

wherein R and $R_1$ are halogen atoms or lower alkyl groups; $R_2$ is a furyl, alkoxyalkyl or alkoxy group; $R_3$ is an alkenyl or propargyl group optionally substituted with halogen atoms or alkyl, haloalkyl, alkoxy, alkoxycarbonyl or aryl groups; and Y is one or more hydrogen or halogen atoms, or alkyl groups.

The invention further provides, as novel chemical compounds, acylanilide derivatives as defined in the above paragraph, and in subsequent paragraphs below.

In a preferred aspect the invention provides a process for combating pests, especially fungi, which comprises applying to plants or seeds, or to their loci, an acylanilide derivative having the formula:

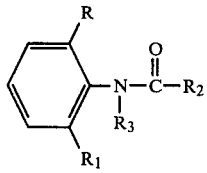

wherein R and $R_1$ are chlorine or methyl, ethyl or propyl and are the same or different; $R_2$ is 2-furyl or a lower alkoxy or lower alkoxy lower alkyl group; and $R_3$ is an alkenyl or propargyl group optionally substituted with a chlorine, bromine or iodine atom, or at least one lower alkyl, lower alkoxy, lower alkoxycarbonyl, halo lower alkyl group or phenyl group.

By the term "lower" is intended alkyl, haloalkyl or alkoxy groups having from 1 to 7 carbon atoms, and preferably from 1 to 4 carbon atoms, and especially methyl, or a methyl group. Preferred alkenyl groups have from 3 to 7 carbon atoms, particularly 3 to 4 carbon atoms, and allyl is especially preferred.

In a particularly preferred aspect the invention provides, as novel chemical compounds, the derivatives having the formulae:

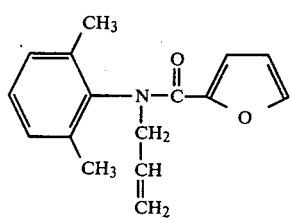

and

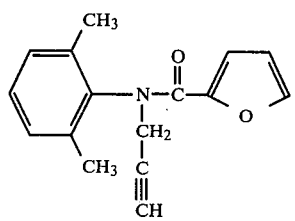

and

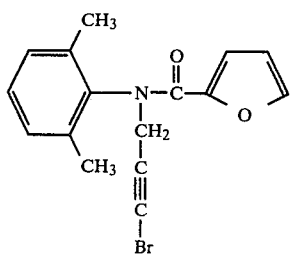

and

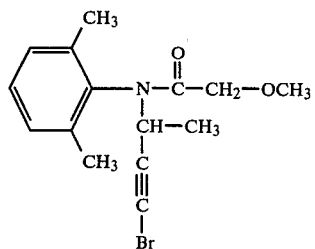

The invention further provides a process for combating pests, especially fungi, and in particular the diseases *Phytophthora infestans* (late blight on potatoes and tomatoes), *Pythium ultimum* (damping off of peas) and *Plasmopara viticola* (downy mildew on vines), which comprises treating plants or seeds, or their loci, with the specific chemical compounds defined in the preceding paragraph.

The invention is illustrated by the specific compounds listed in Tables I and II below. Those in Table I correspond to the general formula:

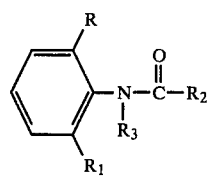

wherein R, $R_1$, $R_2$ and $R_3$ are as indicated in the columns so headed.

TABLE I

| COMPOUND NO | R | $R_1$ | $R_2$ | $R_3$ | m.p. (°C.) |
|---|---|---|---|---|---|
| 1 | $CH_3$ | $CH_3$ |  | $-CH_2CH=CH_2$ | 68–69 |
| 2 | $CH_3$ | $CH_3$ | $-CH_2OCH_3$ | $-CH_2CH=CH_2$ | b.p. 130° C./0.04 mm |
| 3 | $CH_3$ | $CH_3$ | $-CH_2Cl$ | $-CH_2CH=CH_2$ | 74–75 |
| 4 | $CH_3$ | $CH_3$ |  | $-CH(CH_3)CH=CH_2$ | — |
| 5 | $CH_3$ | $CH_3$ | $-CH_2OCH_3$ | $-CH(CH_3)CH=CH_2$ | — |
| 6 | $CH_3$ | $CH_3$ | $-CH_2Cl$ | $-CH(CH_3)CH=CH_2$ | — |
| 7 | $CH_3$ | $CH_3$ |  | $-CH_2-\underset{\underset{CH_3}{\mid}}{C}=CH_2$ | 72–74 |
| 8 | $CH_3$ | $CH_3$ | $-CH_2OCH_3$ | $-CH_2-\underset{\underset{CH_3}{\mid}}{C}=CH_2$ | — |
| 9 | $CH_3$ | $CH_3$ | $-CH_2Cl$ | $-CH_2-\underset{\underset{CH_3}{\mid}}{C}=CH_2$ | — |
| 10 | $CH_3$ | $CH_3$ |  | $-CH_2-CH=CH-CH_3$ | 60–62 |
| 11 | $CH_3$ | $CH_3$ | $-CH_2OCH_3$ | $-CH_2-CH=CH-CH_3$ | — |
| 12 | $CH_3$ | $CH_3$ | $-CH_2Cl$ | $-CH_2-CH=CH-CH_3$ | — |
| 13 | $CH_3$ | $CH_3$ |  | $-CH_2CH=C(CH_3)_2$ | — |
| 14 | $CH_3$ | $CH_3$ | $-CH_2OCH_3$ | $-CH_2CH=C(CH_3)_2$ | — |
| 15 | $CH_3$ | $CH_3$ | $-CH_2Cl$ | $-CH_2CH=C(CH_3)_2$ | — |
| 16 | $CH_3$ | $CH_3$ |  | $-CH_2CH=CH-CH_2Cl$ | 70 |
| 17 | $CH_3$ | $CH_3$ |  | $-CH_2CH=CH-COOCH_3$ (trans isomer) | b.p. 150–170° C. (bulb tube)/0.005 mm > 90% purity by GLC and NMR |
| 18 | $CH_3$ | $CH_3$ |  | $-CH_2-\underset{\underset{Cl}{\mid}}{C}=CH_2$ | 63 |
| 19 | $CH_3$ | $CH_3$ |  | $-CH_2-\underset{\underset{OCH_3}{\mid}}{C}=CH_2$ | 105 |

These alkenyl acylanilide derivatives of the invention can be made, for example, by any of the routes schematically outlined below:

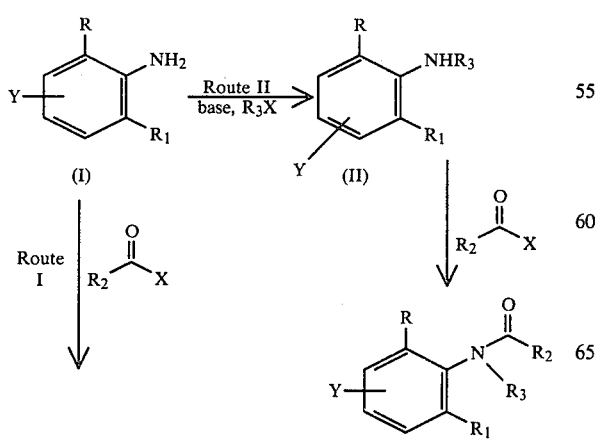

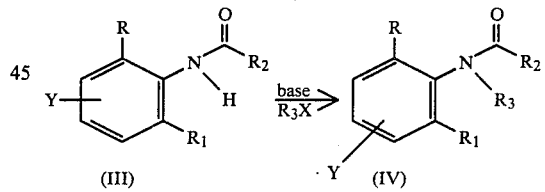

(X = halogen, e.g. Cl, Br)

and exemplified in Example 1 hereinafter. Substitution on the alkenyl group $R_3$ can be effected thereafter.

The invention is further illustrated by the specific compounds listed in Table II below. These correspond to the general formula:

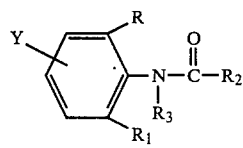

wherein R, $R_1$, $R_2$, $R_3$ and Y are as indicated in the columns so headed.

TABLE II

| COMPOUND NO | R | $R_1$ | $R_2$ | $R_3$ | Y | m.p. (°C.) |
|---|---|---|---|---|---|---|
| 20 | $CH_3$ | $CH_3$ | 2-furyl | $-CH_2C\equiv CH$ | H | 113 |
| 21 | $CH_3$ | $CH_3$ | $CH_2OCH_3$ | $-CH_2C\equiv CH$ | H | 56–57 |
| 22 | $CH_3$ | $CH_3$ | $CH_2Cl$ | $-CH_2C\equiv CH$ | H | 80–81 |
| 23 | $CH_3$ | $CH_3$ | 2-furyl | $-CH(CH_3)-C\equiv CH$ | H | 89–91 |
| 24 | $CH_3$ | $CH_3$ | $-CH_2-OCH_3$ | $-CH(CH_3)-C\equiv CH$ | H | 68–69 |
| 25 | $CH_3$ | $CH_3$ | $-CH_2-Cl$ | $-CH(CH_3)-C\equiv CH$ | H | — |
| 26 | Cl | Cl | 2-furyl | $-CH_2C\equiv H$ | H | 96–98 |
| 27 | Cl | Cl | $-CH_2-OCH_3$ | $-CH_2-C\equiv C-C_6H_5$ | H | — |
| 28 | $CH_3$ | $CH_3$ | 2-furyl | $-CH_2-C\equiv C-Br$ | H | 140–143 |
| 29 | $CH_3$ | $CH_3$ | 2-furyl | $-CH_2-C\equiv C-I$ | H | 121–123 |
| 30 | $CH_3$ | $CH_3$ | $-CH_2-OCH_3$ | $-CH_2-C\equiv C-Br$ | H | 58–59 |
| 31 | $CH_3$ | $CH_3$ | $-CH_2-OCH_3$ | $-CH_2-C\equiv C-I$ | H | 95–98 |
| 32 | $CH_3$ | $CH_3$ | 2-furyl | $-CH_2C\equiv CH$ | Br | 133–134 |
| 33 | $CH_3$ | Cl | 2-furyl | $-CH_2C\equiv CH$ | H | 98–99 |
| 34 | Br | Br | 2-furyl | $-CH_2C\equiv CH$ | Br | 107–111 |
| 35 | $CH_3$ | $CH_3$ | 2-furyl | $-CH(CH_3)C\equiv C-Br$ | H | 103–106 |
| 36 | $CH_3$ | $CH_3$ | $-CH_2-OCH_3$ | $-CH(CH_3)-C\equiv C-Br$ | H | 50–51 |
| 37 | $CH_3$ | $CH_3$ | phenyl | $-CH_2C\equiv C-H$ | H | 89–90 |
| 38 | iso-$C_3H_7$ | iso-$C_3H_7$ | 2-furyl | $-CH_2C\equiv C-H$ | H | 77 |
| 39 | $C_2H_5$ | $C_2H_5$ | 2-furyl | $-CH_2C\equiv C-H$ | H | 86–87 |
| 40 | $CH_3$ | $CH_3$ | 2-furyl | $-CH_2C\equiv C-H$ | $CH_3$ | 94–97 |
| 41 | $CH_3$ | $CH_3$ | $-OCH_2CH_3$ | $-CH_2C\equiv CH$ | H | 68 |

These propargyl acylanilide derivatives of the invention can be made, for example, by any of the routes schematically outlined below:

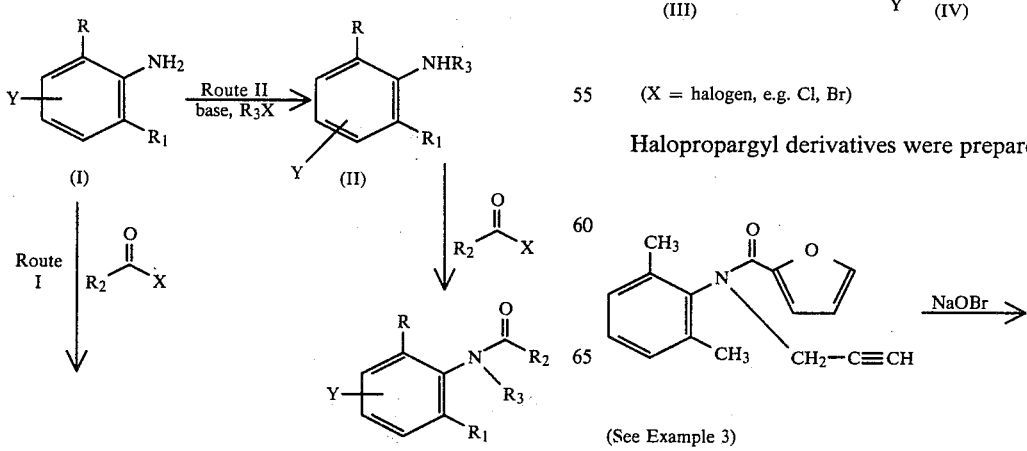

(X = halogen, e.g. Cl, Br)

Halopropargyl derivatives were prepared as follows:

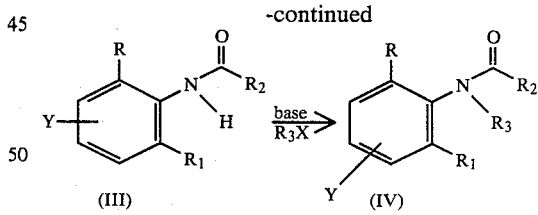

(a)

(See Example 3)

-continued

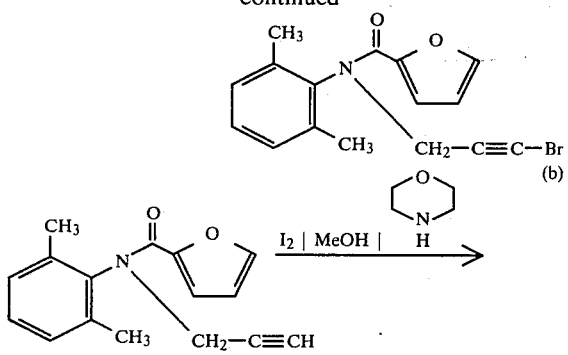

(See Example 4)

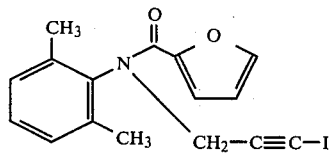

The derivatives and compositions containing them are variously active against a wide range of fungal diseases, particularly, for example against:

(a) *Phytophthora infestans* (late blight) on potatoes and tomatoes
(b) Powdery mildews, for example:
  *Erysiphe graminis* on cereals
  *Sphaerotheca fuliginea* on cucurbits
  *Podosphaera leucotricha* on apples
  *Uncinula necator* on vines
  and other powdery mildews on other hosts
(c) Other fungal diseases, for example:
  *Botrytis cinerea* (grey mould) on tomatoes, strawberries, vines and other hosts
  *Venturia inaequalis* (scab) on apples
  *Plasmopara viticola* (downy mildew) on vines
  *Pythium ultimum* (damping off of peas)
(d) *Cercospora arachidicola* on peanuts and other *Cercospora* species.
(e) Some of the derivatives display activity against the bacterial disease *Xanthomonas oryzae* (bacterial leaf blight) on rice.

A particularly valuable feature of the activity of the acylanilide derivatives is their systemic effect, i.e. their ability to move in a plant to combat an infection or infestation remote from the site of initial application. Thus a derivative, or a composition containing it, may be applied to the soil surrounding the roots of a plant or to the seed or to other plant areas, e.g. leaves, and be taken up by the plant through its roots, or other areas, to combat fungi locally or elsewhere on the plants.

The acylanilide derivatives may be used as such for pesticidal, especially anti-fungal, purposes but are more conveniently formulated into compositions for such usage.

The invention also provides pesticidal, especially fungicidal, compositions comprising as active ingredient an acylanilide derivative as defined in any of the paragraphs above.

The acylanilide derivatives and compositions containing them can be used to combat plant fungi and treat plants or seeds in a number of ways, for example they can be applied, formulated or unformulated, directly to the foilage of a plant which is infected or likely to become infected, or they can be applied also to bushes and trees, to soil or to other medium in which plants, bushes or trees are growing or to be planted, or they can be sprayed on, dusted on or applied as a cream or paste formulation. Application can be to any part of the plant, bush or tree, for example to the foliage, stems, branches, seeds or roots, or to soil surrounding the roots.

The term "treating" as used herein refers to all these modes of application and the term "plant" includes seedlings, bushes and trees. Furthermore, the method of the invention includes protectant, prophylactic and eradicant treatment.

The derivatives are preferably used for agricultural and horticultural purposes in the form of compositions. The type of composition used in any instance will depend upon the particular purpose envisaged.

The compositions may be in the form of dusting powders or granules, for example ordinary grains or "slow release" granules wherein the active ingredient is mixed with a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed may, for example, comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersion or emulsions may be prepared by dissolving the active ingredient(s) in an organic solvent which may contain wetting, dispersing or emulsifying agent(s) and then adding the mixture so obtained to water which may also contain wetting, dispersing or emulsifying agent(s). Suitable organic solvents are ethylene dichloride, isopropyl alcohol, propylene glycol, diacetone alcohol, toluene, kerosene, methylnaphthalene, xylenes and trichloroethylene.

The compositions for spraying may also be in the form of aerosols wherein the formulation is held in a container under pressure in the presence of a propellant, e.g. fluorotrichloromethane or dichlorodifluoromethane.

By including suitable additives, for example additives for improving the distribution, adhesive power and resistance to rain on treated surfaces, the different compositions can be better adapted for various utilities.

The derivatives can be used in smoke generators and also as mixtures with fertilisers (e.g. nitrogen- or phosphorus- containing fertilisers). Compositions comprising only granules of fertiliser incorporating, for example coated with, the derivative, are preferred.

The invention therefore also provides a fertiliser composition comprising the derivative and a fertiliser.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or non-ionic agents. Suitable cationic agents are quaternary ammonium compounds for example, cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain 10–85%, generally 25–60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, for example other fungicides such as dithiocarbamates, dinocap, dichlofluanid and the like, as well as stabilising agent(s), for example epoxides (e.g. epichlorhydrin).

The invention is illustrated by the following Examples wherein the temperatures are in °C.

EXAMPLE 1

This Example illustrates the preparation of Compound No. 1 (Table I) having the structure:

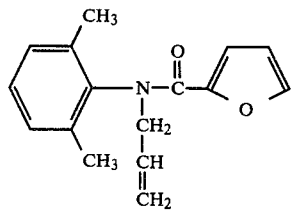

by three different routes I, II and III.

Route I

To 2,6-dimethylaniline (3.0 g, 0.025 mole) in methylenedichloride (30 ml) was added triethylamine (2.6 g, 0.026 mole), the mixture cooled in ice-water and 2-furoyl chloride (3.3 g, 0.025 mole) added dropwise with stirring. The mixture was stirred at 20° C. for 1 hour, poured into water, the organic layer separated, dried (MgSO$_4$), filtered and solvent evaporated to give a solid which was recrystallised from methylenedichloride/light petrol to give a colourless crystalline solid, m.p. 125°–126° C. (4.6 g, 86%), characterised by i.r., n.m.r. and elemental analysis as N-2-furoyl 2,6-dimethylanilide.

To sodium hydride (0.3 g, 0.0125 mole) in dimethylformamide (30 ml) was added solid N-2-furoyl 2,6-dimethylanilide (2.17 g, 0.0125 mole) with stirring. After the evolution of hydrogen had ceased (ca. 30 minutes), allyl bromide (1.5 g, 0.0125 mole) was added, the mixture stirred for 2 hours, then poured into water, filtered and the solid recrystallised from light petrol to give N-(2,6-dimethylphenyl)-N-allyl-2-furancarboxamide (2.5 g, 80%) as colourless needles, m.p. 68°–69° C.; n.m.r. gave τ 2.62 (5-furyl CH), 2.82 (phenyl CHs), 3.84 (4-furyl CH), 4.06 (allyl C$\underline{H}$=CH$_2$), 4.60 (3-furyl CH), 4.88 and 4.92 (allyl C$\underline{H}_2$=CH—), 5.64 (allyl —C$\underline{H}_2$—CH=CH$_2$) and 7.83 (2,6-dimethylphenyl). Elemental analysis gave: Found C 75.30, H 6.85, N 5.45. Calculated for C$_{16}$H$_{17}$NO$_2$: C 75.25, H 6.70, N 5.50%.

Compound No. 17 was prepared similarly with the exception that the solvent used during the alkylation stage was toluene instead of dimethylformamide.

Route II 2,6-Dimethylaniline (12.1 g, 0.1 mole) and allyl chloride (3.8 g, 0.05 mole) were mixed and heated over a steam bath using an efficient reflux condenser for 8 hours, then treated with aqueous caustic soda solution, extracted with ether, the ethereal layer worked up and the residue distilled to give 2,6-dimethylphenyl allylamine, b.p. 5355°/0.3 mm) (6.0 g, 75%).

To 2,6-dimethylphenyl allylamine (4.0 g, 0.025 mole) in methylenedichloride (50 ml) was added triethylamine (2.6 g, 0.025 mole), the mixture was cooled in ice-water and 2-furoyl chloride (3.3 g, 0.025 mole) added dropwise with stirring. The mixture was stirred for 2 hours at 20° C. then poured into water (100 ml), the organic layer separated, dried (MgSO$_4$) and solvent removed at reduced pressure to give a solid which was recrystallised from light petrol to give colourless needles, m.p. 68°–69° C., identical with that obtained by Route I.

Route III

Allyl p-toluenesulphonate (10.6 g, 0.05 mole) was heated with 2,6-dimethylaniline (6.0 g, 0.05 mole) in a steam bath for 2 hours, poured into water (100 ml), extracted into methylenedichloride (50 ml), dried (MgSO$_4$), filtered, solvent evaporated and the product distilled to give 2,6-dimethylphenyl allylamine, identical with that in Route II. Subsequent steps were the same as for Route II.

EXAMPLE 2

This Example illustrates the preparation of Compound No. 20 of Table II, namely the compound having the structure:

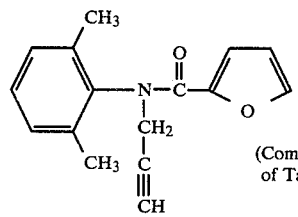

(Compound No. 20 of Table II)

by three different routes.

Route I

To 2,6-dimethylaniline (3.0 g, 0.025 mole) in methylenedichloride (30 ml) was added triethylamine (2.6 g, 0.026 mole), the mixture cooled in ice-water and 2-furoyl chloride (3.3 g, 0.025 mole) added dropwise with stirring. The mixture was stirred at 20° C. for 1 hour, poured into water, the organic layer separated, dried (MgSO₄), filtered and solvent evaporated to give a solid which was recrystallised from methylenedichloride/light petrol to give a colourless crystalline solid, m.p. 125°–126° C. (4.6 g, 86%), characterised by i.r., n.m.r. and elemental analysis as N-2-furoyl 2,6-dimethylanilide.

To sodium hydride (0.3 g, 0.0125 mole) in dimethylformamide (30 ml) was added solid N-2-furoyl 2,6-dimethylanilide (2.17 g, 0.0125 mole) with stirring. After the evolution of hydrogen had ceased (ca. 30 minutes), propargyl bromide (1.5 g, 0.0125 mole) was added, the mixture stirred for 2 hours, then poured into water, filtered and the solid recrystallised from light petrol to give N-(2,6-dimethylphenyl)-N-propargyl-2-furancarboxamide (3.3 g, 90%) as colourless needles, m.p. 113° C. (10.1 g, 80%), $\nu_{max}$ 3250, 3100. 1630 cm⁻¹ (in nujol); n.m.r. gave $\tau$2.46 (singlet, 5-furyl CH), 2.80 (singlet, phenyl CHs), 3.80 (multiplet, 4-furyl CH), 4.5 (doublet, 3-furyl CH), 5.50 (doublet, CH₂), 7.60 (triplet, C≡CH) and 7.80 (singlet, 2,6-dimethylphenyl). Elemental analysis gave:

Found: C 75.5, H 6.1, N 5.4%; Calculated for C₁₆H₁₅NO₂: C 75.8, H 6.0, N 5.4%.

Route II 2,6-Dimethylaniline (12.1 g, 0.1 mole) and propargyl chloride (3.8 g, 0.05 mole), were mixed and heated over a steam bath using an efficient reflux condenser for 8 hours, then treated with aqueous caustic soda solution, extracted with ether, the ethereal layer worked up and the residue distilled to give 2,6-dimethylphenyl propargylamine, b.p. 56°–58° C./0.01 mm.

To 2,6-dimethylphenyl propargylamine (8.0 g, 0.05 mole) in methylenedichloride (50 ml) was added triethylamine (5.1 g, 0.05 mole), the mixture cooled in ice-water and 2-furoyl chloride (6.5 g, 0.05 mole) added dropwise with stirring. The mixture was stirred 2 hours at 20° C. then poured into water (100 ml), the organic layer separated, dried (MgSO₄) and solvent removed at reduced pressure to give a solid which was recrystallised from light petrol to give colourless needles m.p. 113° C.

Route III

Propargyl p-toluenesulphonate (6.0 g, 0.05 mole) was heated with 2,6-dimethylaniline (6.0 g, 0.05 mole) on steam bath for 2 hours, poured into water (100 ml), extracted into methylenedichloride (50 ml), dried (MgSO₄), filtered, solvent evaporated and the product distilled to give 2,6-dimethylphenyl propargylamine, identical with that in Route II. Subsequent preparative steps were as outlined in Route II.

EXAMPLE 3

This Example illustrates the preparation of Compound No. 28 of Table II, namely, N-(2,6-dimethylphenyl)-N-(3-bromoprop-2-ynyl)-2-furancarboxamide, having the structure:

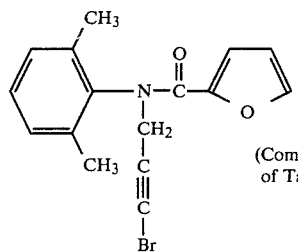

(Compound No. 28 of Table II)

Bromine (3.4 g, 1.1 ml) was added to sodium hydroxide (4.0 g) dissolved in water (35 ml) at 0°–5° C., then N-(2,6-dimethylphenyl)-N-propargyl-2-furancarboxamide (2.5 g) dissolved in glyme (20 ml) was added to the stirred mixture. After the addition, the mixture was stirred at 10° C. for 30 minutes and at 20° C. for 1 hour, poured into cold water (250 ml), the precipitated solid filtered and recrystallised from light petrol to yield the title compound (2.6 g, 79%), m.p. 140°–143° C. I.r. showed bands at $\nu_{max}$ 2220 and 1640 cm⁻¹, and elemental analysis gave C=57.96, H=4.20, N=4.14 and Br=23.40 (calculated for C₁₆H₁₄NO₂Br: C=57.85, H=4.25, N=4.22 and BR=24.06%).

EXAMPLE 4

This Example illustrates the preparation of Compound No. 29 of Table II, namely, N-(2,6-dimethylphenyl)-N-(3-iodoprop-2-ynyl)-2-furancarboxamide, having the structure:

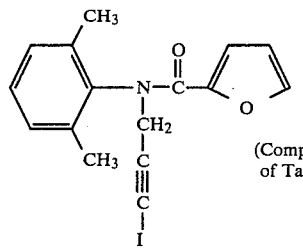

(Compound No. 29 of Table II)

Iodine (10.0 g) was dissolved in methanol (150 ml) then morpholine (40 ml) added. To this solution was added N-(2,6-dimethylphenyl)-N-propargyl-2-furancarboxamide (10.4 g) dissolved in methanol (70 ml) and the mixture stirred at 20° C. for 6 hours,* then methanol removed at reduced pressure, water (500 ml) and ether (500 ml) added, the ethereal phase separated, washed with aqueous sodium sulphite, dried (MgSO₄), filtered, solvent removed at reduced pressure and the residual solid recrystallised from light petrol to give the title compound (8.7 g), m.p. 121°–123° C.

(* Subject to T.L.C.)

Compounds Nos. 30 and 31 of Table II, namely, N-2,6-dimethylphenyl)-N-(3-bromoprop-2-ynyl)-methoxymethylcarboxamide and N-(2,6-dimethylphenyl)-N-(3-iodoprop-2-ynyl)-methoxymethylcarboxamide, were prepared by similar methods.

EXAMPLE 5

This Example illustrates the preparation of Compound No. 23 of Table II, namely the compound having the formula:

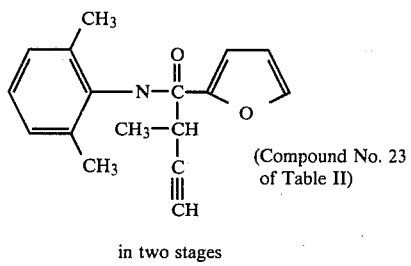

(Compound No. 23 of Table II)

in two stages

Stage 1. The method reported for similar amines in G. F. Hennion and R. S. Hanzel, J. Amer-Chem-Soc., 1960, 82, 4908 was used to prepare N-(2,6-Dimethylphenyl)-N-2(but-3-ynyl)amine having the formula:

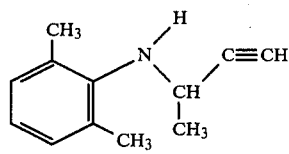

To a mixture of 2,6-dimethylphenylamine (111 ml), triethylamine (167 ml), ether (300 ml) and water (75 ml) stirred at 20° C. under nitrogen was added cuprous chloride (0.9 g) and copper bronze (0.9 g) followed by 2-chlorobut-3-yne (89 ml) in ether (75 ml) added dropwise over 1 hour and the whole mixture stirred another 2 hours, maintaining the temperature at 20° C. The mixture was then poured into ether (400 ml) and water (200 ml), the ethereal layer separated, the aqueous layer extracted with ether (2×300 ml), the combined ethereal layer washed with water (300 ml), dried ($K_2CO_3$), the ether evaporated and the residue distilled to give 37.5 g (30%) product b.p. 60°–61°/0.1 mm., m.p. 32°–33° C.

Stage 2. The compound (Compound No. 23 of Table II) N-(2,6-Dimethylphenyl)-N-2(but-3-ynyl)-N-2-furancarboxamide having the formula:

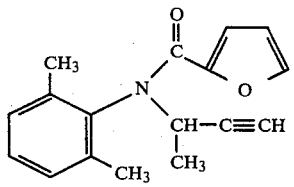

was then prepared as follows.

To N-(2,6-dimethylphenyl)-N-2(but-3-ynyl)amine (9.1 g) and pyridine (4.3 ml) in methylene dichloride (100 ml) was added 2-furoyl chloride (5.2 ml) dropwise with cooling at 10° C., the mixture was allowed to warm to room temperature and stirred for 2 hours, then diluted with methylene dichloride (100 ml), washed with water (100 ml), dried ($MgSO_4$), solvent stripped and the solid recrystallised from light petrol to give 10.5 g of the product, m.p. 89°–91° C.; calculated for $C_{17}H_{17}NO_2$: C=76.4, H=6.37, N=5.24; found: C=75.9, H=6.49, N=5.3%; N.m.r. gave $(CDCl_3)\nu_{max}$ 3255, 2120 and 1640 cm$^{-1}$; $\tau$ 8.49 d($CH_3$—CH—), 7.81 d ($CH_3$),

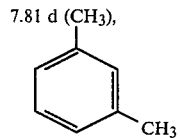

4.77 q($CH_3$—CH—), 4.63 q(furyl), 3.88 m(furyl), 2.67 d(furyl) and 2.85 s(phenyl).

EXAMPLE 6

This Example illustrates the preparation of Compound No. 24 of Table II, namely the compound N-(2,6-Dimethylphenyl)-N-2(but-3-ynyl)-N-methoxymethylcarboxamide

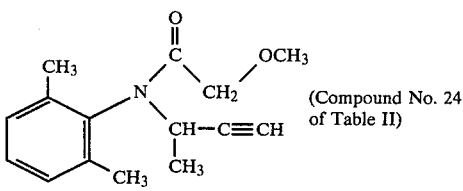

(Compound No. 24 of Table II)

Following the procedure described in Stage 2 of Example 4 N-(2,6-dimethylphenyl)-N-2(but-3-ynyl)amine (12.87 g), methoxyacetyl chloride (6.8 ml) and pyridine (6 ml) were reacted together to give 10.9 g of the product, m.p. 68°–69° C., N.m.r. gave $(CDCl_3)_{max}$ 3250, 3290, 2120 and 1680 cm$^{-1}$.

EXAMPLE 7

This Example illustrates the preparation of Compound No. 35 of Table II, namely the compound N-(2,6-Dimethylphenyl)-N-(2(4-bromobut-3-ynyl)-N-2-furancarboxamide, having the formula:

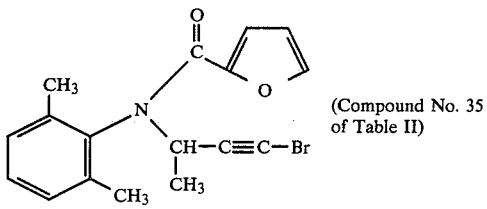

(Compound No. 35 of Table II)

To a sodium hypobromite solution prepared from bromine (1.15 ml) and sodium hydroxide (3.6 g) in water (15 ml) at 10° C. was added dropwise with stirring over 30 minutes N-(2,6-dimethylphenyl)-N-2(but-3-ynyl)-N-2-furancarboxamide (2.67 g) in glyme (20 ml), maintaining the temperature at 10° C. The mixture was then allowed to warm up to room temperature and stirred for 2 hours, then diluted with water (250 ml), the solid filtered, dried and recrystallised from light petrol to give 3.0 g of the product, m.p. 103°–6° C.; calculated for $C_{17}H_{16}NO_2Br$: C=58.96, H=4.62, N=4.05. Found: C=58.94, H=4.5, N=3.85%; N.m.r. gave $(CDCl_3)$-$\nu_{max}$ 2220 and 1622 cm$^{-1}$; $\tau$ 8.54 d($\underline{CH}_3$—CH—), 7.82 d ($CH_3$),

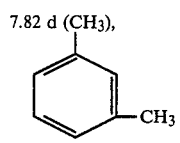

4.73 (CH$_3$—C$\underline{\underline{H}}$—), 4.65 d(furyl), 3.89 m(furyl), 2.66 d(furyl) and $\overline{2.87}$ s(phenyl).

EXAMPLE 8

This Example illustrates the preparation of Compound No. 36 of Table II, namely the compound N-(2,6-Dimethylphenyl)-N-2(4-bromobut-3-ynyl)-N-methoxymethylcarboxamide having the formula

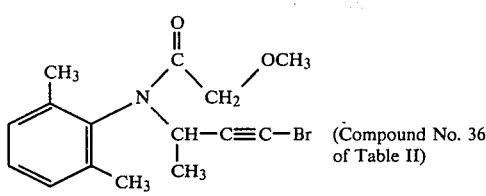

As Example 5 from N-(2,6-dimethylphenyl)-N-2(but-3-ynyl)-N-methoxymethylcarboxamide and sodium hypobromite solution to give the product, m.p. 50°–51° C.; N.m.r. gave (CDCl$_3$)-$v_{max}$ 2215 and 1673 cm$^{-1}$; $\tau$ 8.54 d(C$\underline{\underline{H}}_3$—CH—),

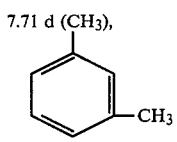

7.71 d (CH$_3$), 6.64 s(—O—CH$_3$), 6.48 s(—CH$_2$—), 4.72 q(CH$_3$—CH—) and 2.81 s(phenyl).

EXAMPLE 9

An emulsifiable concentrate was made up by mixing the ingredients, and stirring the mixture until all the constituents were dissolved.

| Compound No 35 of Table II | 10% |
| --- | --- |
| Ethylene dichloride | 40% |
| Calcium dodecylbenzenesulphate | 5% |
| "Lubrol" L | 10% |
| "Aromasol" H | 35% |

EXAMPLE 10

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44–100, to obtain the desired size of grains.

| Compound No 35 of Table II | 50% |
| --- | --- |
| "Dispersol" T | 25% |
| "Lubrol" APN 5 | 1.5% |
| Sodium acetate | 23.5% |

EXAMPLE 11

The ingredients were all ground together to produce a powder formulation readily dispersible in liquids.

| Compound No 35 of Table II | 45% |
| --- | --- |
| "Dispersol" T | 5% |
| "Lissapol" NX | 0.5% |

| -continued | |
| --- | --- |
| "Cellofas" B600 | 2% |
| Sodium acetate | 47.5% |

EXAMPLE 12

The active ingredient was dissolved in a solvent and the resultant liquid was sprayed on to the granules of China clay. The solvent was then allowed to evaporate to produce a granular composition.

| Compound No 35 of Table II | 5% |
| --- | --- |
| China clay granules | 95% |

EXAMPLE 13

A composition suitable for use as a seed dressing was prepared by mixing the three ingredients.

| Compound No 35 of Table II | 50% |
| --- | --- |
| Mineral oil | 2% |
| China clay | 48% |

EXAMPLE 14

A dusting powder was prepared by mixing the active ingredient with talc.

| Compound No 35 of Table II | 5% |
| --- | --- |
| Talc | 95% |

EXAMPLE 15

A Col formulation was prepared by ball-milling the constituents set out below and then forming an aqueous suspension of the ground mixture with water.

| Compound No 35 of Table II | 40% |
| --- | --- |
| "Dispersol" T | 10% |
| "Lubrol" APN5 | 1% |
| Water | 49% |

EXAMPLE 16

A dispersible powder formulation was made by mixing together the ingredients set out below and then grinding the mixture until all were thoroughly mixed.

| Compound No 35 of Table II | 25% |
| --- | --- |
| "Aerosol" OT/B | 2% |
| "Dispersol" A.C. | 5% |
| China clay | 28% |
| Silica | 40% |

EXAMPLE 17

This Example illustrates the preparation of a dispersible powder formulation. The ingredients were mixed and the mixture then ground in a comminution mill.

| Compound No 35 of Table II | 25% |
| --- | --- |
| "PERMINAL" BX | 1% |
| "Dispersol" T | 5% |
| Polyvinylpyrrolidone | 10% |

-continued

| | |
|---|---|
| Silica | 25% |
| China clay | 34% |

EXAMPLE 18

The ingredients set out below were formulated into a dispersible powder by mixing then grinding the ingredients.

| | |
|---|---|
| Compound No 35 of Table II | 25% |
| "Aerosol" OT/B | 2% |
| "Dispersol" A | 5% |
| China clay | 68% |

In Examples 8 to 18 the proportions of the ingredients given are by weight and the Examples were all repeated using, as active ingredient, Compound Nos. 1, 20, 21, 23, 24, 28, 29 and 36.

There now follows an explanation of the compositions or substances represented by the various Trade Marks and Trade Names mentioned above.

| | |
|---|---|
| LUBROL L: | a condensate of nonyl phenol (1 mole) with ethylene oxide (13 moles) |
| AROMASOL H: | a solvent mixture of alkyl-benzenes |
| DISPERSOL T AND AC: | a mixture of sodium sulphate and a condensate of formaldehyde with sodium naphthalene sulphonate |
| LUBROL APN 5: | a condensate of nonyl phenol (1 mole) with naphthalene oxide (5.5 moles) |
| CELLOFAS B600: | a sodium carboxymethyl cellulose thickener. |

EXAMPLE 19

Compounds of Table I and II were tested against a variety of foliar fungal diseases of plants. The technique employed was as follows.

The plants were grown in John Innes Potting Compost (No. 1, or No. 2, as appropriate) in 4 cm diameter minipots. A layer of fine sand was placed at the bottom of the pot to facilitate uptake of test compound by the roots.

The test compounds were formulated either by bead-milling with aqueous Dispersol T or as a solution in acetone/ethanol which was diluted to the required concentration immediately before use. For the tests conducted, 100 ppm a.i. suspensions were sprayed on to the foliage and applied to the roots of the same plant via the soil. (Sprays were applied to maximum retention, and root drenches to a final concentration equivalent to approximately 40 ppm a.i./dry soil). An exception is the test on Plasmopara viticola in which the chemical is applied to the foliage only.

For the tests, the test compound was applied to the soil (roots) and to the foliage (by spraying) one or two days before the plant was inoculated with the diseases. After inoculation, the plants were put into an appropriate environment to allow infection to take place and then incubated until the disease was ready for assessment. The period between inoculation and assessment varied from 3 to 13 days according to the disease and environment, as shown in Table III below.

TABLE III

| | DISEASE AND PLANT | INTERVAL USUAL TIME (DAYS)* |
|---|---|---|
| (1) | Phytophthora infestans (tomato) | 3 |
| (2) | Plasmopara viticola (vine) | 6 |
| (3) | Cercospora arachidicola (peanut) | 13 |

*N.B. These intervals are not rigid and will vary with the individual tests. Assessment is normally done at the point of optimum disease development commensurate with a practical timetable.

The disease control was recorded by the following gradings:

| |
|---|
| 4 = No disease |
| 3 = 0–5% |
| 2 = 6–25% |
| 1 = 26–60% |
| 0 = >60% |

The results are shown in Table IV.

TABLE IV

| COMPOUND NO | PHYTOPHTHORA INFESTANS (tomato) | PLASMOPARA VITICOLA (vine) | CERCOSPORA ARACHIDICOLA (peanut) |
|---|---|---|---|
| 1 | 3 | 4 | — |
| 2 | 4 | 2 | — |
| 3 | 3 | 0 | — |
| 7 | 1 | 0 | — |
| 10 | 4 | 2 | — |
| 17 | 1 | 2 | 0 |
| 18 | 3 | 2 | 0 |
| 19 | 3 | 0 | 0 |
| 20 | 4 | — | — |
| 21 | 4 | 4 | — |
| 22 | 3 | 3 | 1 |
| 23 | 4 | 4 | 1 |
| 26 | 3 | 3 | 3 |
| 28 | 4 | 4 | 1 |
| 29 | 4 | 4 | 1 |
| 30 | 4 | 3 | 0 |
| 31 | 4 | 4 | 2 |
| 32 | 0 | 0 | 0 |
| 33 | 3 | 3 | — |
| 34 | 1 | 0 | 1 |
| 35 | 4 | 4 | 0 |
| 36 | 4 | 4 | 0 |
| 37 | 3 | 3 | 0 |

TABLE IV-continued

| COMPOUND NO | PHYTOPHTHORA INFESTANS (tomato) | PLASMOPARA VITICOLA (vine) | CERCOSPORA ARACHIDICOLA (peanut) |
| --- | --- | --- | --- |
| 38 | 3 | 0 | 0 |
| 39 | 2 | 0 | 0 |
| 40 | 3 | 0 | 0 |
| 41 | 2 | 0 | 0 |

EXAMPLE 20

This Example illustrates the activity of the acylanilide derivatives of the invention against the disease *Pythium ultimum*.

Batches of pea seeds (30 seeds per batch) of the variety Kelvedon Wonder were dressed with 30 mg and 15 mg amounts for solid chemicals or 15 mg and 7.5 mg amounts for liquid chemicals of a powdered formulation containing the test chemical so as to apply to the seed on a weight/weight basis (i.e. milligrams of active chemical per kilogram of seed) 500 ppm (parts per million) and 250 ppm, respectively, of the test chemical.

The formulations used for test chemicals which were solids were a mixture, by weight, of 12.5% test chemical and 87.5% China clay. For test chemicals which were liquids the formulations contained 25% by weight of test chemical and 75% by weight of China clay.

Compost infected with the disease organism was prepared as follows. A bulk inoculum of the disease was made by mixing 200 grams of washed silver sand with 4 grams of maize meal and then mixing in 40 milliliters of de-ionised water. This was then placed in an autoclave at 121° C. for 20 minutes, cooled and then inoculated with one quarter of a 7-day old agar plate (potato dextrose) culture of *Pythium ultimumu* incubated at 22° C. The culture was added to a mixture of 18 liters of vermiculite, 160 grams of "BEMAX" and 4 liters of water to form the infected compost and this was thoroughly mixed and then incubated at 22° C. for 24 hours.

Square pots (7 cm) were half-filled with potting compost and thirty seeds spread between 3 replicate pots which were then topped up with the infected vermiculite-based compost. The pots were then watered lightly and placed in a glasshouse maintained at 15° to 20° C. until the seedlings emerged (approximately 2 weeks after sowing).

Assessment was carried out by counting the number of emerged seedlings and the number of healthy seedlings, adding these two totals together, and then expressing the figure obtained as a percentage of the same figure obtained for uninfected control seedlings. The percentage values were then converted into 0 to 4 grade assessments (as set out in Example 19) and these are given in Table V below:

TABLE V

| COMPOUND NUMBER | DISEASE GRADE |
| --- | --- |
| 21 (Table II) (a solid chemical) | 4 |
| 24 (Table II) (a liquid chemical) | 4 |

I claim:

1. A fungicidal acylanilide derivative having the formula:

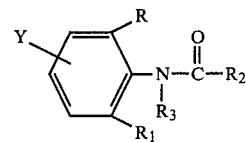

wherein R and $R_1$ are halogen atoms or lower alkyl groups; $R_2$ is a furyl or alkoxyalkyl group; and $R_3$ is an alkenyl or propargyl group optionally substituted with halogen atoms or alkyl, haloalkyl, alkoxy, alkoxycarbonyl or aryl groups; and Y is one or more hydrogen or halogen atoms, or alkyl groups.

2. An acylanilide derivative having the formula:

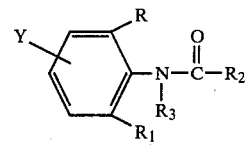

wherein R and $R_1$ are chlorine or methyl, ethyl or propyl, and are the same or different; $R_2$ is a 2-furyl, or a lower alkoxy lower alkyl group; and $R_3$ is an alkenyl or propargyl group optionally substituted with a chlorine, bromine or iodine atom, or at least one lower alkyl, lower alkoxy lower alkoxy carbonyl, halo lower alkyl or phenyl group.

3. An acylanilide derivative as defined in claim 1 and wherein when any of R, $R_1$ and $R_3$ and Y are alkyl, alkenyl, alkynyl, alkoxy or alkoxyalkyl groups, or are substituted by alkyl, haloalkyl, alkoxy or alkoxycarbonyl groups, these groups, and substituent groups, contain up to seven carbon atoms.

4. An acylanilide derivative having the formulae:

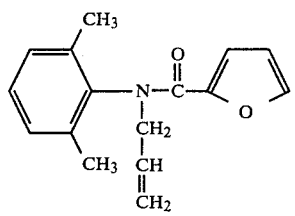

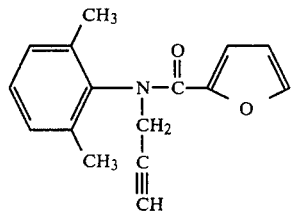

-continued

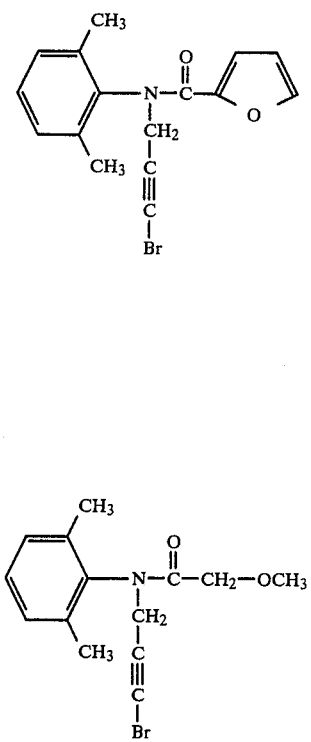

5. An acylanilide derivative having the formula:

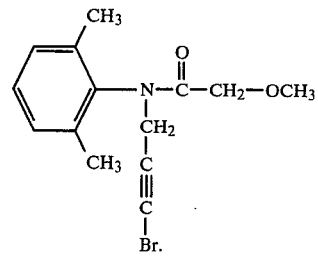

6. A compound of the formula

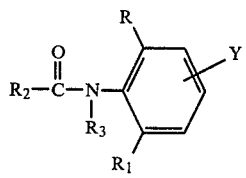

wherein
R₂ is furyl or alkoxyalkyl,
R₃ is a propargyl group optionally substituted by halogen, alkyl, alkoxycarbonyl or aryl,
R and R₁ are halogen or alkyl, and
Y is one or more hydrogen, halogen or alkyl.

7. A pesticidal, especially plant anti-fungal and anti-bacterial, composition comprising as an active ingredient, an acylanilide derivative as defined in claim 1, and an inert carrier for said acylanilide derivative.

8. A process for combating pests, especially plant fungi and plant bacteria, which comprises applying to plants or seeds, or to their loci, an acylanilide derivative as defined in claim 1.

9. A process for combating pests, especially fungi, and in particular the diseases *Phytophthora infestans* (late blight on potatoes and tomatoes), *Erysiphe graminis* (powdery mildew on cereals), and *Plasmopara viticola* (downy mildew on vines), which comprises treating plants or seeds, or their loci, with an acylanilide derivative as defined in claim 1.

* * * * *